United States Patent [19]

US 7,732,185 B2
Jun. 8, 2010

(12) United States Patent
Kitamura et al.

(10) Patent No.: US 7,732,185 B2
(45) Date of Patent: Jun. 8, 2010

(54) PLASMID HAVING RESPONSE TO DIOXINS, TRANSGENIC CELL FOR MEASURING DIOXINS, DIOXINS SENSING METHOD AND BIOSENSOR USING THE SAME

(75) Inventors: Masanori Kitamura, Yamanashi (JP); Shuichiro Maeda, Yamanashi (JP)

(73) Assignee: Yamanashi University, Kofu-shi (JP)

( * ) Notice: Subject to any disclaimer, the term of this patent is extended or adjusted under 35 U.S.C. 154(b) by 595 days.

(21) Appl. No.: 11/597,407

(22) PCT Filed: May 16, 2005

(86) PCT No.: PCT/JP2005/008875

§ 371 (c)(1),
(2), (4) Date: Apr. 16, 2007

(87) PCT Pub. No.: WO2005/113767

PCT Pub. Date: Dec. 1, 2005

(65) Prior Publication Data

US 2008/0050766 A1   Feb. 28, 2008

(30) Foreign Application Priority Data

May 24, 2004   (JP)   .............................. 2004-153293

(51) Int. Cl.
*C12N 1/20* (2006.01)
*C12N 15/00* (2006.01)
(52) U.S. Cl. .................. 435/252.3; 435/320.1; 435/194
(58) Field of Classification Search .............. 435/252.3, 435/320.1, 194
See application file for complete search history.

(56) References Cited

FOREIGN PATENT DOCUMENTS

| JP | 2004-135662 A | 5/2004 |
|----|---------------|--------|
| JP | 2005-237326 A | 9/2005 |
| KR | 2001-046920 A | 6/2001 |

OTHER PUBLICATIONS

Borge et al. [Gene 223:213-219 (1998)].*
Behnisch et al., Environment International, vol. 27, pp. 413-439 (2001).
Nao Yokoyama et al., Eisei Yakugaku Kankyo Technology Koen Yoshishu, vol. 2003, Oct. 10, 2003, p. 96.
Nao Yokoyama et al., Nippon Naibunpi Kakuran Kagaku Busshitsu Gakkai Kenkyu Happyokai Yoshishu, vol. 6, Dec. 2, 2003, p. 204.
Shigenori Shinba et al., Forum 2001: Eisei Yakugaku Kankyo Toxicology Koen Yoshishu Heisei 13 Nen, Oct. 15, 2001, p. 68.
Jones et al., Proc. Natl. Acad. Sci. USA, vol. 83, No. 9, 1986, pp. 2802 to 2806.

(Continued)

*Primary Examiner*—Tekchand Saidha
(74) *Attorney, Agent, or Firm*—Birch, Stewart, Kolasch & Birch, LLP

(57) ABSTRACT

A plasmid comprising a gene, which is reactive with dioxins and/or polycyclic aromatic hydrocarbons to thereby be activated (hereinafter referred to as DRE gene), and a secretory marker protein expressing gene disposed understream of the DRE gene. Further, there is developed a transgenic cell having this plasmid introduced therein which when exposed to dioxins and/or polycyclic aromatic hydrocarbons, secretes a secretory marker protein. Still further, there is developed a biosensor utilizing this transgenic cell.

6 Claims, 14 Drawing Sheets

OTHER PUBLICATIONS

Holmes et al., Mol. Pharmacol. 1997, vol. 52, No. 2, 1997, pp. 202-211.

De Benedetti et al., Nucleic Acids Research, vol. 19, No. 8, Apr. 25, 1991, pp. 1925 to 1932.

James RI et al., Biotechnol Bioeng., vol. 67, No. 2, Jan. 20, 2000, pp. 134 to 140.

Kasai et al., Anal Biochem, vol. 337, No. 1, Feb. 1, 2005, pp. 84 to 88.

Kasai et al., The Molecular Biology Society of Japan Nenkai Program Koen Yoshishu, vol. 27, Nov. 25, 2004, p. 1026.

Kasai et al., Anal Biochem, vol. 335, No. 1, Dec. 1, 2004, pp. 73 to 80.

Dertinger, S. et al. "Influence of aromatic hydrocarbon receptor-mediated events on the genotoxicity of cigarette smoke condensate", Carcinogenesis, vol. 19 No. 11 pp. 2037-2042. 1998. XP-002476407.

Dertinger, S. et al. "Aryl hydrocarbon receptor signaling plays a significant role in mediating benzo[a]pyrene- and cigarette smoke condensate- induced cytogenetic damage in vivo" Carcinogenesis, vol. 22 No. 1 pp. 171-177, 2001. XP-002476408.

Muto, H. et al. "Dioxins in Cigarette Smoke", Archives of Environmental Health, Washington D.C., US, May/Jun. 1989 vol. 44 No. 3 p. 171-174. XP-003007303.

Kasai, A. et al. "High Levels of Dioxin-Like Potential in Cigarette Smoke Evidencedby In Vitro and In Vivo Biosensing" Cancer Res., 2006 vol. 66 No. 14. p. 7143-7150. XP009098585.

Kasai, A. et al. "Direct, Continuous Monitoring of Air Pollution by Transgenic Sensor Mice Responsive to Halogenated and Polycyclic Aromatic Hydrocarbons", Environmental Health Perspectives, vol. 116, No. 3, p. 349-354, 2008. XP-002476409.

Kitamura, M. et al. "Cigarette smoke as a trigger for the dioxin receptor-mediated signaling pathway", Cancer Letters, vol. 252, 2007, p. 184-194. XP-002476410.

Behnisch, P. "Bioanalytical screening methods for dioxins and dioxin-like compunds- a review of bioassay/biomarker technology", Environmental Internationsl vol. 27, 2001 p. 413-439. XP-002979004.

Cullen, B. et al. "Secreted Placental Alkaline Phosphates as a Eukaryotic Reporter Gene" Methods in Enzymology, vol. 216, 1992, p. 362-368.

Nao Yokoyama et al., Eisei Yakugaku Kankyo Toxicology Koen Yoshishu, vol. 2003, Oct. 10, 2003, p. 96.

Garrison et al., Fundam Appl Toxicol. 1996, vol. 30, No. 2, pp. 194-203.

* cited by examiner

PLASMID HAVING RESPONSE TO DIOXINS, TRANSGENIC CELL FOR MEASURING DIOXINS, DIOXINS SENSING METHOD AND BIOSENSOR USING THE SAME

TECHNICAL FIELD

The present invention relates to a simplified fast high-sensitive method of sensing or determining a hazardous chemical substance based on the fact that an endocrine disrupter, part of carcinogen and the like such as dioxins and polycyclic aromatic hydrocarbon acts via an aryl hydrocarbon receptor (hereinafter, abbreviated as AhR) that is an intracellular receptor, sensing substance, and a dioxins sensing biosensor.

BACKGROUND ART

In order to establish measures against environmental pollution that is one of serious problems of modern society, it is necessary to accurately assess a degree of exposure to a hazardous chemical substance in the environment. It is thus indispensable that a method has been established of analyzing a hazardous chemical substance with ease, high sensitivity and high reproducibility.

Even a minute level of dioxins causes various kinds of hazardous action. Accordingly, the establishment of the method of sensing dioxins sharply and quickly is thought to be an urgent issue to assess exposure to dioxins accurately and prevent health problems. Further, it is a significant issue to totally and quantitatively assess biological toxicity of polycyclic aromatic hydrocarbon that is a hazardous substance in the environment as well as dioxins, and tobacco smoke including polycyclic aromatic hydrocarbon and dioxins as a complex.

Typical methods of sensing dioxins and the like in the environment include a method using an endogenous biomarker such as, for example, cytochrome P-4501A1 that is a drug metabolizing enzyme, bioassay using cultured cells, enzyme immunoassay, method using chromatography, and the like. Particularly, the bioassay using gene engineering techniques has recently attracted attention due to the convenience and high sensitivity.

Such a gene-engineering bioassay is comprised of some basic units. The basic units are two i.e. (1) cell and (2) gene structure integrated into the cell. The gene structure is comprised of a dioxins responsive DNA sequence that is a DNA sequence functioning as a sensor for dioxins, and a marker protein gene that specifies a marker protein.

By introducing the gene structure to a cell to stably integrate into chromosome DNA of the cell, it is possible to generate a sensor cell reacting with dioxins and the like.

When such a transgenic cell is exposed to a sample including dioxins or the like, the dioxins or the like first react with AhR in the cell, and further, form a complex with a coactivator (hereinafter abbreviated as Arnt) that is a transcription promoting coupling factor, and the complex activates the dioxins responsive DNA sequence as a transcription factor. As a result, expression of the marker protein gene is accelerated downstream of the gene sequence.

By expression of the marker protein gene, the maker protein is produced, and by quantitatively determining the protein, it is possible to assess that what concentration of dioxins or the like exists in the sample.

As the marker protein gene, used conventionally are enzyme genes such as chloramphenicol acetyl transferase, β-galactosidase, luciferase and the like, and green fluorescent protein genes.

However, the conventional bioassay has problems that (1) since a marker protein is not secreted, the operation is required of cutting the cell to extract the marker protein for determination of the protein, (2) the sensitivity is not sufficient in sensing a minute level of a hazardous substance in the environment, and even in the high-sensitive system, 1 pM is a sensing limit in terms of 2,3,7,8-tetrachlorodibenzo-p-dioxin (hereinafter, abbreviated as TCDD), (3) two or three days are required for a bioassay, (4) 60,000 to 100,000 cells are required for one sample, and therefore, costs such as cultivation costs and personnel costs are high. Particularly, items (2) to (4) are serious problems in efficiently screening a large number of samples.

Non-patent Document 1: P. A. Behnisch, K. Hosoe, S. Sakai, Bioanalytical screening methods for dioxins and dioxin-like compounds: a review of bioassay/biomarker technology, Environ. Int. 27 (2001) 413-439.

Non-patent Document 2: Japanese Patent Application No. 2004-135662 "Dioxins measurement transformant and sensing method, quantitative analysis method and screening method for dioxins using the transformant"

DISCLOSURE OF INVENTION

Problems to be Solved by the Invention

Therefore, the objects of the invention are (1) simplification of bioassay processes, (2) improvement in sensing sensitivity, (3) great reduction in bioassay time, and (4) reduction in costs such as cultivation costs and personnel costs, as compared with the conventional bioassay for sensing dioxins using luciferase and green fluorescent protein.

Means for Solving the Problem

The invention is a dioxins and/or polycyclic aromatic hydrocarbon responsive plasmid such that a secretory marker protein gene is integrated into downstream of a dioxins and/or polycyclic aromatic hydrocarbon high-sensitive gene sequence that reacts with dioxins and/or polycyclic aromatic hydrocarbon to be activated.

It is suitable that the secretory marker protein is a secreted alkaline phosphatase gene.

The invention is a transgenic cell for measuring dioxins and/or polycyclic aromatic hydrocarbon such that the dioxins and/or polycyclic aromatic hydrocarbon responsive plasmid is introduced to a cultivated cell highly expressing an aromatic hydrogen receptor, the aromatic hydrogen receptor binds with the dioxins and/or polycyclic aromatic hydrogen, and the secretory marker protein is produced.

It is suitable that the cultivated cell highly expressing an aromatic hydrogen receptor is Hepa-1c1c7.

The invention enables a biosensor using the transgenic cell for measuring dioxins and/or polycyclic aromatic hydrocarbon as a sensor for sensing dioxins and/or polycyclic aromatic hydrocarbon.

The invention is a dioxins and/or polycyclic aromatic hydrocarbon sensing method for exposing a transgenic cell for measuring dioxins and/or polycyclic aromatic hydrocarbon to dioxins and/or polycyclic aromatic hydrocarbon, determining activity of a secretory marker protein secreted from the transgenic cell, and sensing the dioxins and/or polycyclic aromatic hydrocarbon, where the transgenic cell is prepared by introducing a dioxins and/or polycyclic aromatic hydrocarbon responsive plasmid, having a dioxins and/or polycyclic aromatic hydrocarbon high-sensitive gene sequence that reacts with dioxins and/or polycyclic aromatic hydrocarbon to be activated and a secretory marker protein gene integrated into downstream of the gene sequence, to a cell highly expressing an aromatic hydrogen receptor.

It is suitable that the secretory marker protein is a secreted alkaline phosphatase gene. It is further suitable that the cell is Hepa-1c1c7.

The invention is a method of quantitatively assessing biological toxicity of tobacco smoke for exposing a transgenic cell for measuring dioxins and/or polycyclic aromatic hydrocarbon to tobacco smoke, determining activity of the secretory marker protein secreted from the transgenic cell, and assessing biological toxicity of tobacco smoke, where the transgenic cell is prepared by introducing a dioxins and/or polycyclic aromatic hydrocarbon responsive plasmid, having a dioxins and/or polycyclic aromatic hydrocarbon high-sensitive gene sequence that reacts with dioxins and/or polycyclic aromatic hydrocarbon to be activated and a secretory marker protein gene integrated into downstream of the gene sequence, to a cell highly expressing an aromatic hydrogen receptor.

It is suitable that the secretory marker protein is a secreted alkaline phosphatase gene.

Advantageous Effect of the Invention

According to the invention, by simple chemical emission measurement and the like, it is possible to measure dioxins and/or polycyclic aromatic hydrocarbon with ease.

Further, it is possible to complete the dioxin measurement processes between inoculation of cells and measurement within a few hours. Furthermore, according to the invention, it is possible to measure dioxins and/or polycyclic aromatic hydrocarbon with high sensitivity at low cost.

The invention is an excellent invention enabling sensing of dioxins and/or polycyclic aromatic hydrocarbon contained in air, river, soil, food and living appliances.

Best Mode for Carrying Out the Invention

A best embodiment for carrying out the invention will be described below.

EXAMPLE 1

FIG. 1 is a diagram illustrating a structure of a dioxins and/or polycyclic aromatic hydrocarbon reactive plasmid, pDRE-SEAP10. PDRE-SEAP10 is comprised of a dioxins high-sensitive DNA sequence (hereinafter, abbreviated as MMTV-DRE11) obtained by integrating a dioxins responsive DNA sequence (hereinafter, abbreviated as DRE) into part of a promoter of mouse mammary tumor virus (hereinafter, abbreviated as MMTV), secreted alkaline phosphatase (hereinafter, abbreviated as SEAP) gene 12 positioned downstream of DRE, and polyadenylation signal (hereinafter, abbreviated as polyA13) derived from simian virus 40 (hereinafter, abbreviated as SV40).

Conventionally, DRE has been used as a dioxins responsive DNA sequence. In this Example, as a sensor DNA sequence for sensing dioxins, used is MMTV-DRE obtained by integrating DRE into part of MMTV. A high-sensitive assay system is thereby established.

MMTV-DRE11 is obtained by integrating four DREs known to be activated in response to dioxins into part of a promoter of MMTV, and has strong response to dioxins, as compared with DRE alone.

FIG. 2 shows a result of examination on comparison in sensor potential between MMTV-DRE and DRE. SEAP reporter plasmids having MMTV-DRE or only DRE as a sensor sequence were prepared, and each of the plasmids was gene-introduced to a Hepa-1c1c7 cell. In addition, details of gene introduction will be described later. The cells were stimulated by TCDD, and increases in SEAP activity were compared. In the cell to which was introduced the SEAP reporter plasmid only having DRE as a sensor sequence, the SEAP activity increased by 4.5 times by the stimulus of TCDD.

In contrast thereto, in the cell (Hepa 1c1c7-DRE-SEAP cell, hereinafter, referred to as an HeDS cell) to which was introduced the SEAP reporter plasmid having MMTV-DRE as a sensor sequence, the SEAP activity increased by 43.2 times by the stimulus of TCDD. In the cell to which was introduced the SEAP reporter plasmid only having MMTV as a sensor sequence, the SEAP activity did not increase by the stimulus of TCDD. This means that the sequence of MMTV strongly amplifies the response of DRE to dioxin. The high reactivity of MMTV-DRE enables a fast assay with low cost.

In Example 1, SEAP was used as a marker protein. Including SEAP, any bioassay systems for dioxins using a secretory marker protein have not been established conventionally. SEAP is a maker protein enabling sensing of dioxins with high sensitivity as luciferase, but is secreted outside the cell as distinct from luciferase, and thus, eliminates the need of operation for cutting the cell to extract the protein.

FIG. 3 is a graph of measurement of sensing sensitivity of TCDD with 5,000 HeDS cells. In the conventional dioxin assay using luciferase, 60,000 to 100,000 cells are required to sense 1 pM of TCDD. In contrast thereto, as shown in FIG. 3, it is possible to sense 0.5 pM of TCDD using 5,000 HeDS cells.

By using SEAP as a marker protein, dioxins can be assayed only using such a minute amount as 5 µl of sample of the conditioned medium. There is a very high correlation between the transfer level of SEAP gene 12 and the secretory level of SEAP protein, and the activity can be detected and determined easily by a chemical emission detection system such as a luminometer. In addition, polyA13 is an indispensable gene sequence in the process where messenger RNA is produced and translated to a protein.

pDRE-SEAP10 is prepared by a typical method of gene processing. In other words, a piece of MMTV-DRE11 that is cut by a restricted enzyme and purified is integrated into upstream of the SEAP gene 12 of the SEAP plasmid without a promoter using T4DNA ligase.

The T4DNA ligase is an enzyme for coupling a 5' end 3' end of adjacent DNA strands. The prepared pDRE-SEAP10 is introduced to *Escherichia coli* to increase in large numbers, and is purified by the typical method of gene processing.

The prepared pDRE-SEAP is gene-introduced to the Hepa-1c1c7 cell that is a mouse liver cancer cell strain by procedures as in FIG. 4, and stable recombination cells are established. Herein, the inventors have selected the Hepa-1c1c7 cell from viewpoints that (1) to establish a bioassay system for dioxins, it is indispensable to use a cell that produces an aryl hydrocarbon receptor (hereinafter, abbreviated as AhR), and that (2) to establish a high-sensitive assay system, it is an essential requirement to select a cell highly expressing AhR.

As a result of keen examination from the viewpoints, the inventors have selected Hepa-1c1c7 that is a cell system derived from liver cancer cell. FIG. 4 shows the procedures for introducing the prepared pDRE-SEAP to the Hepa-1c1c7 cell and establishing a stable recombination cell.

Removed $4 \times 10^6$ Hepa-1c1c7 cells from a culture dish with trypsin are rinsed well with PBS that is phosphate buffered saline, and placed in a cuvette (Bio-Rad Laboratories, Product No. 165-2088) for electroporation (S1). Plasmid pcDNA3.1 containing 20 μg of pDRE-SEAP and 2 μg of neomycin-resistant gene is added to the cells and mixed, and the resultant is kept standing in ice for 10 minutes (S2).

Electroporation is next performed using a Gene Pulser (Bio-Rad Laboratories) on conditions of 150 mV and 960μF, and a number of cells one-tenth to one-twenties the cells are seeded on 100 mm-culture dish, and cultured at 37° C. in the presence of 5% of $CO_2$ and 10% of fetal bovine serum (hereinafter, abbreviated FBS) for three days (S3).

A-MEM (Gibco Industries, Inc. Product No. 12561-056) was used as a culture medium. Then, by culturing in the presence of 500 μg/ml of neomycin for one to two weeks, non-recombination cells are killed (S4), and only recombination cells that pDRE-SEAP is stably integrated into the chromosome DNA survive, grow and form a clump.

Each cell clump is treated with trypsin to be removed, transferred to a 96-well culture plate every two wells, and cultured for one week continuously (S5). After the cells become confluent, the culture medium of each well is exchanged with 100 μl of α-MEM containing 1% FBS, and the cells are cultured for 24 hours in the presence or absence of 10 pM TCDD. Then, using 5 μl of the conditioned medium, a predetermined SEAP assay is performed to establish HeDS cells that react with a low concentration of dioxin with the highest sensitivity, and the cells are used for a dioxins sensing bioassay (S6). In this specification, the bioassay method is referred to as DRE-based Sensing of dioxin via Secreted Alkaline phosphatase (hereinafter, abbreviated as the DRESSA method).

FIG. 5 shows the response mechanism of the established HeDS cell to dioxins. In the HeDS cell, into the chromosome DNA is stably integrated each component of pDRE-SEAP10 i.e. MMTV-DRE11, and in its downstream, SEAP gene 12 and polyadenylation signal 13. When the cell is exposed to dioxins 20, the dioxins 20 is first passed through the cell membrane, and is bound with AhR14 present in the cytoplasm.

Further, AhR14 forms a complex with Arnt15 that is a coactivator, enters the nuclear, and is combined with MMTV-DRE11 to activate. As a result, transcription of downstream SEAP gene 12 is promoted, messenger RNA 16 is produced and translated to protein 18 with ribosome 17, and the protein is promptly secreted outside the cell as a SEAP protein. Accordingly, by measuring the activity of the SEAP protein in the conditioned medium, it is possible to determine a level of dioxins to which the cells are exposed. Procedures of sensing dioxins in a sample are shown in FIG. 6 as a flowchart. First, HeDS cells with a concentration of $2 \times 10^4$/well are seeded in each well of a 96-well culture plate. As a culture medium, 100 μl of A-MEM containing 1% PBS is filled into each well (S1). After the cells are cultured for 24 hours to be fixed to the bottom of each well, the culture medium is exchanged, and 1 μl of a liquid sample containing TCDD is added (S2). After culturing for 24 hours, the conditioned medium is sampled every 5 μl (S3), and the SEAP protein activity is measured by procedures as described below.

The SEAP protein activity in the conditioned medium is determined as described below. To 5 μl of the conditioned medium is added 15 μl of buffer, the resultant is incubated at 65° C. for 30 minutes, and endogenous alkaline phosphatase activity is inactivated. Added further is 20 μl of buffer containing L-homoarginine that is an inhibitor of endogenous alkaline phosphatase, and the resultant is kept standing for 5 minutes. Then, 15 μl of substrate CSPD is added thereto, the resultant is kept standing at a dark place for 30 minutes, and the degree of chemical emission is measured by a luminometer.

FIG. 7 shows a result that HeDS cells were stimulated with 6 pM of TCDD, and transition of the SEAP protein activity in the culture medium was traced with time up to 10 hours. Used as a control was dimethyl sulfoxide (hereinafter, abbreviated as DMSO) that is a solvent of TCDD. Significant increases are observed four hours after TCDD addition, and the activity increases gradually with time.

FIG. 8 shows a result of subsequent transition of the SEAP protein activity up to 72 hours. It is understood that increases in the SEAP protein activity continued for 48 hours, and then, reached equilibrium.

FIG. 9 shows a result of examination of the sensitivity of HeDS cells. HeDS cells were exposed to TCDD with a low concentration of 0 to 1 pM, and increases in the SEAP protein activity in the culture medium were examined. Significant increases in the SEAP protein activity were already observed in 0.25 pM (250 fM).

Thus, the DRESSA method is capable of sensing TCDD with a concentration of 1 pM or less that is regarded as the sensing limit of the conventional bioassay. In addition, the inventors confirmed that the SEAP protein activity increases in the culture medium while being dependent on the concentration up to 100 pM.

FIG. 10 shows a result of examination on the number of cells required for the DRESSA method. In other words, a number of cells as shown in the graph were seeded in a 96-well culture plate, the cells were exposed to 1 nM of TCDD, and then, the SEAP protein activity in the culture medium was measured. As shown in FIG. 10, it was clarified that when 50 cells exist in one sample (one well), 1 nM of TCDD can be sensed sufficiently. The number corresponds to 1/1000 to 1/2000 the number of cells, 60,000 to 100,000/well, required for the conventional assay.

EXAMPLE 2

In order to perform the above-mentioned DRESSA method easily and economically in a short time, it is possible to simplify the sensing procedures as described above, as shown in FIG. 1a. In other words, 50 μl of the culture medium containing 1 μl of sample is filled into each well of a 96-well culture plate, and immediately, HeDS cells floated in the culture medium are added (total 100 μl) (S1).

The conditioned medium is sampled three to four hours later (S2), and the SEAP protein activity is measured (S3). By using this scheme, it is possible to sense 1 pM of TCDD regarded as the sensing limit of the current method within four to five hours. Hereinafter, this method is referred to as a fast DRESSA method. The fast DRESSA method has no difference in sensing sensitivity from the DRESSA method.

FIG. 12 shows a result that HeDS cells were stimulated with TCDD (6 pM and 1 nM) by the fast DRESSA method, and transition of the SEAP protein activity in the culture medium was traced with time. In each case, significant increases were already observed at the time three hours has elapsed since addition of TCDD, and the activity increased gradually with time.

FIG. 13 shows a result of examination of comparison in the sensitivity between the DRESSA method and fast DRESSA method.

The same number of cells was exposed to 6 pM of TCDD on the fixing condition in the DRESSA method, and on the floating condition in the fast DRESSA method. Then, increases in the SEAP protein activity in the conditioned medium were compared and examined with time. As a result, as shown in FIG. 13, any differences were not recognized between both the methods in the sensing sensitivity of dioxins up to 24 hours after stimulation.

FIG. 14 shows the SEAP protein activity in the culture medium after HeDS cells were stimulated by 1 μM of each of 3-methylcholanthrene (3-MC), benzo[a]pyrene (B[a]P) and β-naphthoflavone (βNF) that are polycyclicaromatic hydrocarbons. Each case shows remarkable induction of the SEAP protein activity, as compared with DMSO as control stimulus. Thus, the HeDS cell reacts with 3-MC, B [a]P, and βNF that are hazardous chemical substances, as well as dioxins with which action is made via AhR, and secretes the SEAP protein.

EXAMPLE 3

The tobacco smoke contains combined hazardous chemical substances such as dioxins, polycyclic aromatic hydrogen and the like. AhR bound with such hazardous chemical substances in the tobacco smoke is bound with DRE, and exhibits biological toxicity. It is possible to express the AhR activating potential of tobacco smoke as a value in terms of an amount of TCDD that causes comparable AhR activation. By assuming the converted value to be a DRE-activating potential value (hereinafter, abbreviated as a DAP value) and using the value as an index, the AhR activating potential of tobacco smoke was quantitatively assessed. In addition, the assessing method is extremely useful in determining the degree of effect of smoking on health.

Using five brands of cigarettes respectively with tar content of 1, 6, 10, 14 and 20 mg/piece, the smoke of each cigarette is produced with an aspiration rate of 10.5 l/min, and the smoke corresponding to a piece of cigarette is dissolved in 50 ml of PBS.

HeDS cells are seeded in a 96-well culture plate in 5000 cells/well, and a diluent of 100 to 1000 times the tobacco smoke extract (five kinds, n=4 in each) is added. As a chemical substance to be a reference, 1 to 100 pM of TCDD is similarly added. After culturing for 16 hours, the conditioned medium is taken every 5 μl, and the SEAP activity is measured.

The calibration curve is generated that represents the correlation between the TCDD concentration and SEAP activity, the concentration of the hazardous substance in each tobacco smoke extract is calculated in terms of TCDD, and the total AhR activating potential contained in the smoke generated from a piece of each cigarette is calculated and expressed as a DAP value. Table 1 shows the DAP values. As shown in Table 1, the tobacco smoke shows extremely high AhR activating potential. In addition, there is a positive correlation between the tar content and DAP value, but when cigarettes respectively with tar content of 1 mg and 20 mg are compared with each other, the DAP value of the cigarette of 1 mg-tar content is not 1/20 that of the cigarette of 20 mg-tar content, but only about 1/3. Further, the DAP value of the brand with the tar content of 14 mg is inversely higher than that of the brand with the tar content of 20 mg. These facts mean that the tar content typically used as an index of the effect on health is not sufficient as an index of biological toxicity, and the significance of the DAP value is high as a more practical new index.

TABLE 1

| Brand | Tar content (mg) | DAP value (ng TCDD-comparable/piece) |
|---|---|---|
| Mild Seven (one) | 1 | 30.6 ± 7.5 |
| Mild Seven (super lights) | 6 | 51.2 ± 6.4 |
| Mild Seven (original) | 10 | 81.6 ± 8.0 |
| Seven Star | 14 | 100.8 ± 20.8 |
| Piece | 20 | 95.2 ± 5.2 |

INDUSTRIAL APPLICABILITY

The invention enabling dioxins and dioxin-like hazardous chemical substance to be sensed easily, fast, inexpensively and with high sensitivity has a high utility value in industry such as monitoring of wastewater, drink water control, food quality control, monitoring of contamination of endocrine disrupter in an industrial product, and the like.

Figure 1:
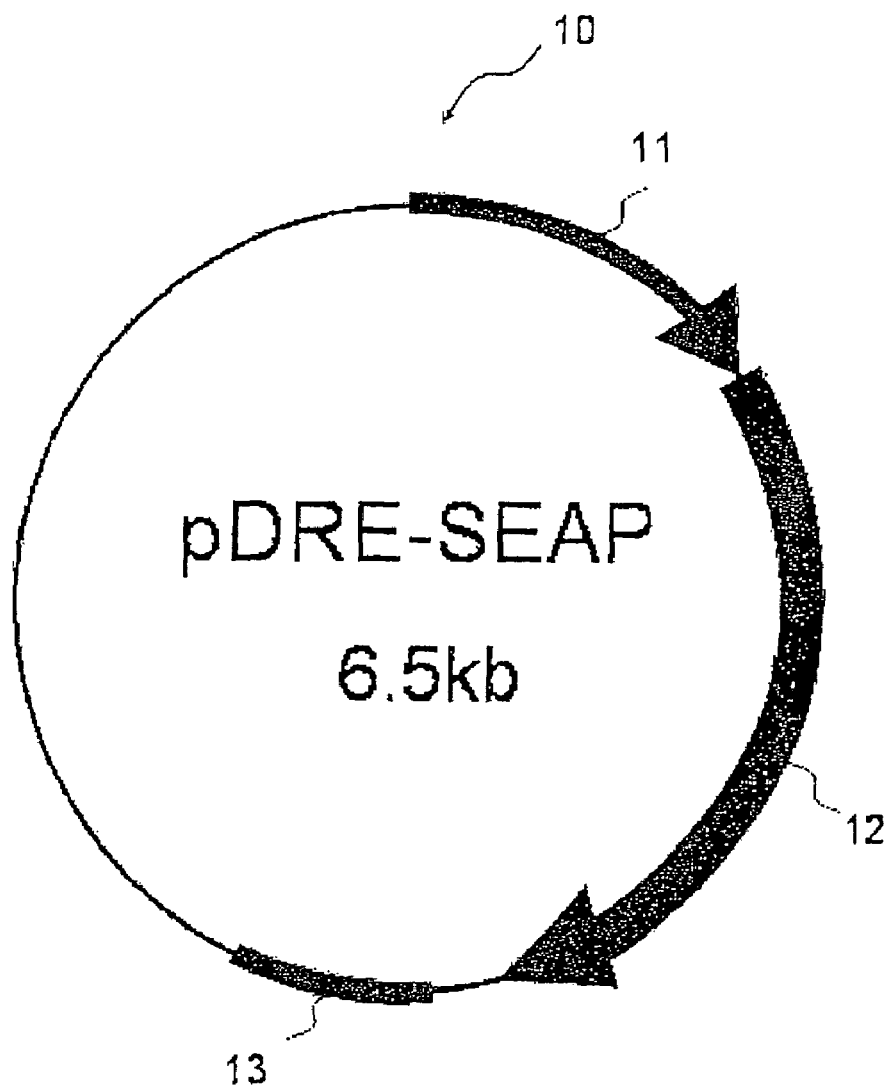
FIG. 1 shows a structure of a dioxins and dioxin-like substance responsive plasmid (pDRE-SEAP)
Figure 2:
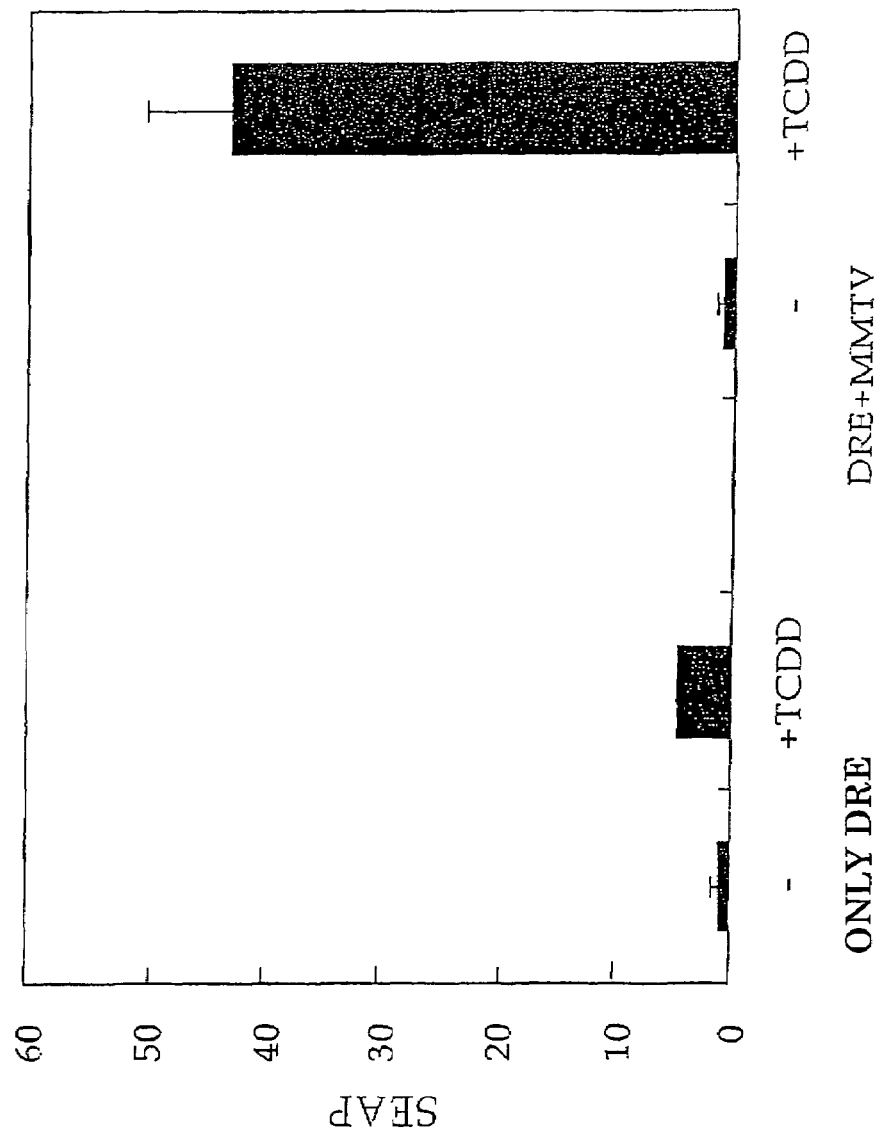
FIG. 2 shows a result of examination on comparison in sensor potential between MMTV-DRE and DRE.
Figure 3:
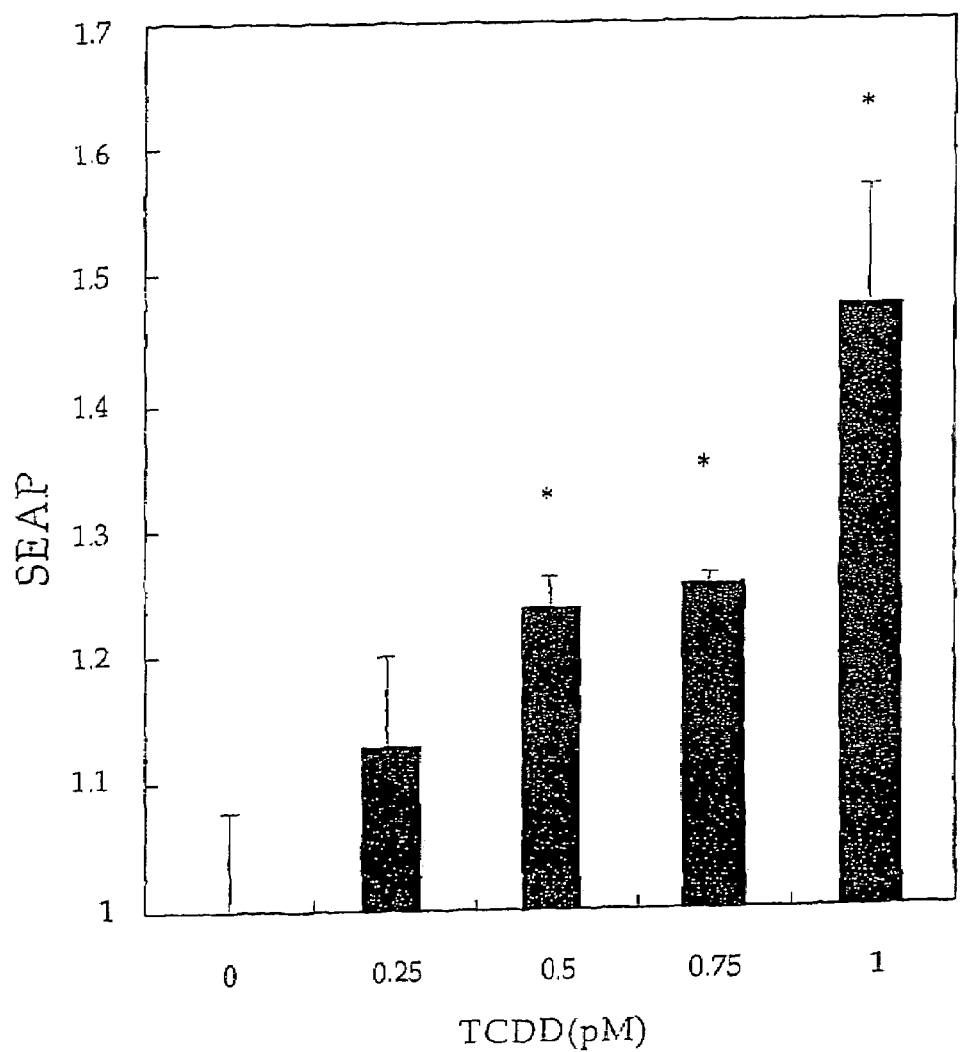
FIG. 3 is a graph of measurement of sensing sensitivity of TCDD with 5,000 HeDS cells.
Figure 4:
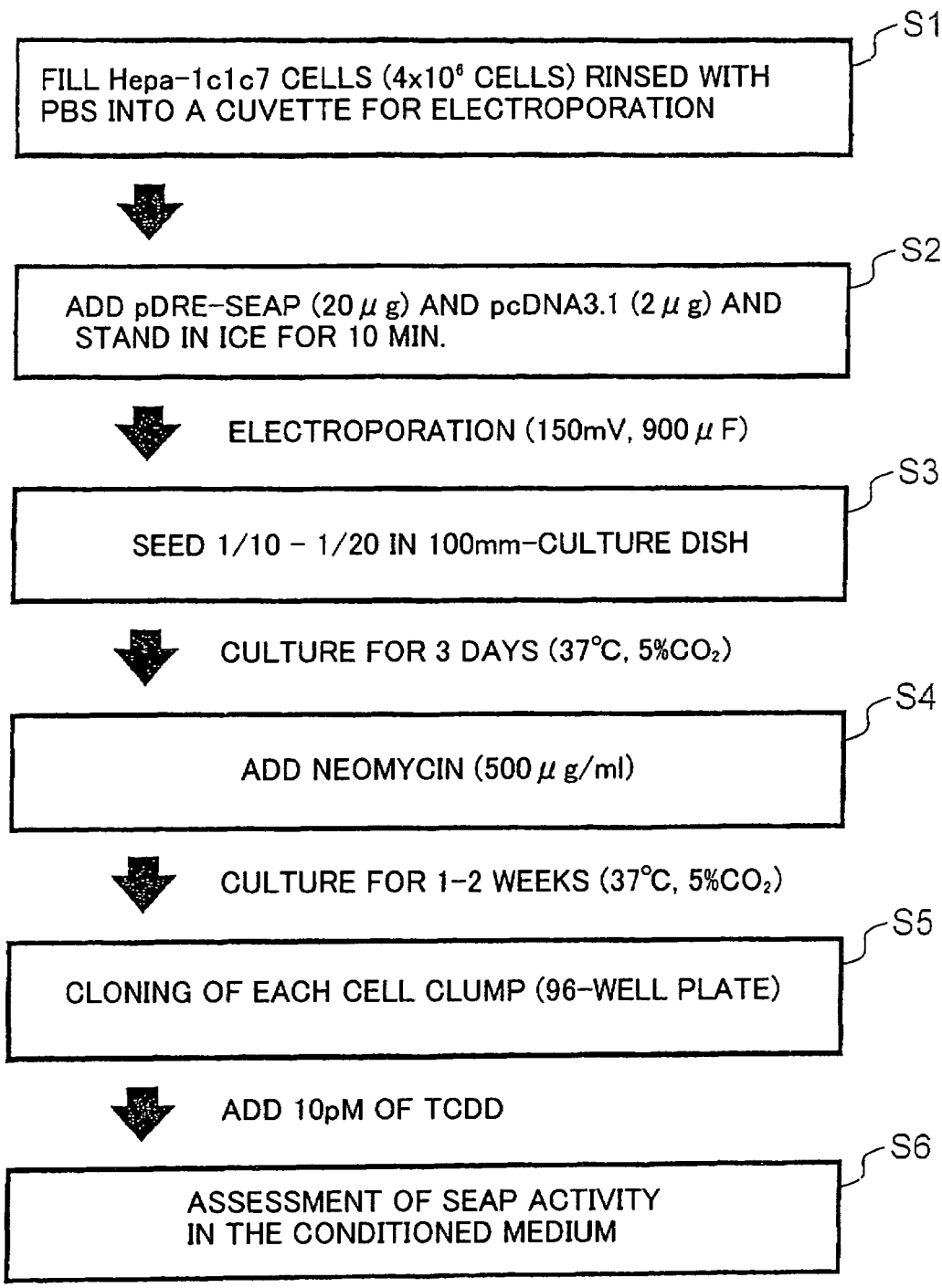
FIG. 4 shows procedures of establishing an HeDS cell.
Figure 5:
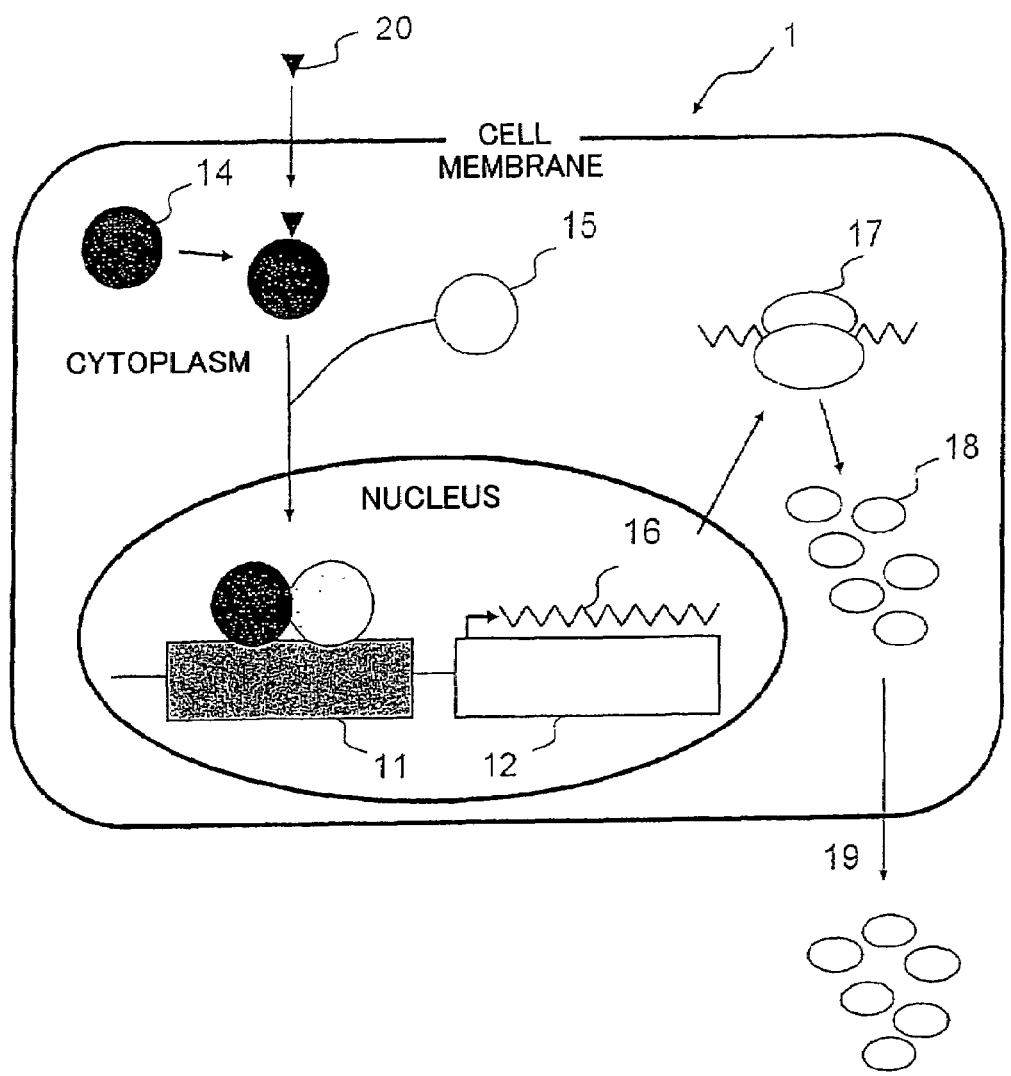
FIG. 5 shows a dioxins sensing mechanism of the HeDS cell.
Figure 6:
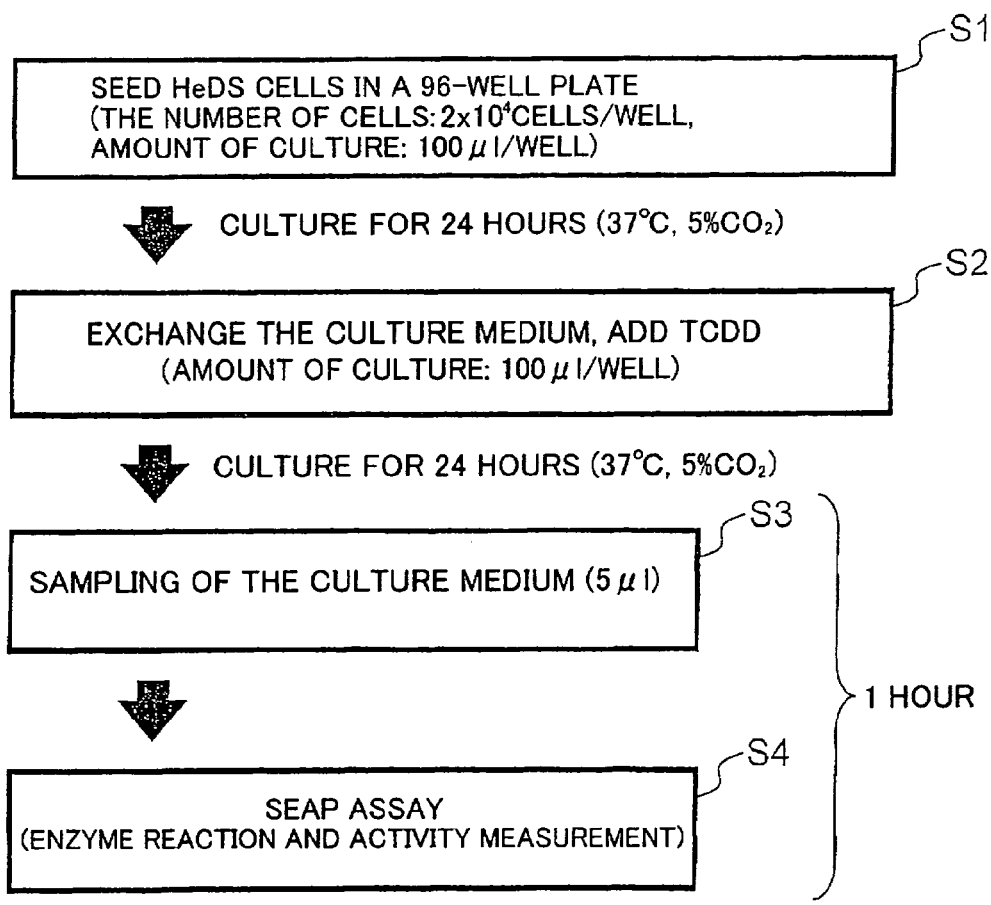
FIG. 6 shows procedures of sensing dioxins by the DRESSA method.
Figure 7:
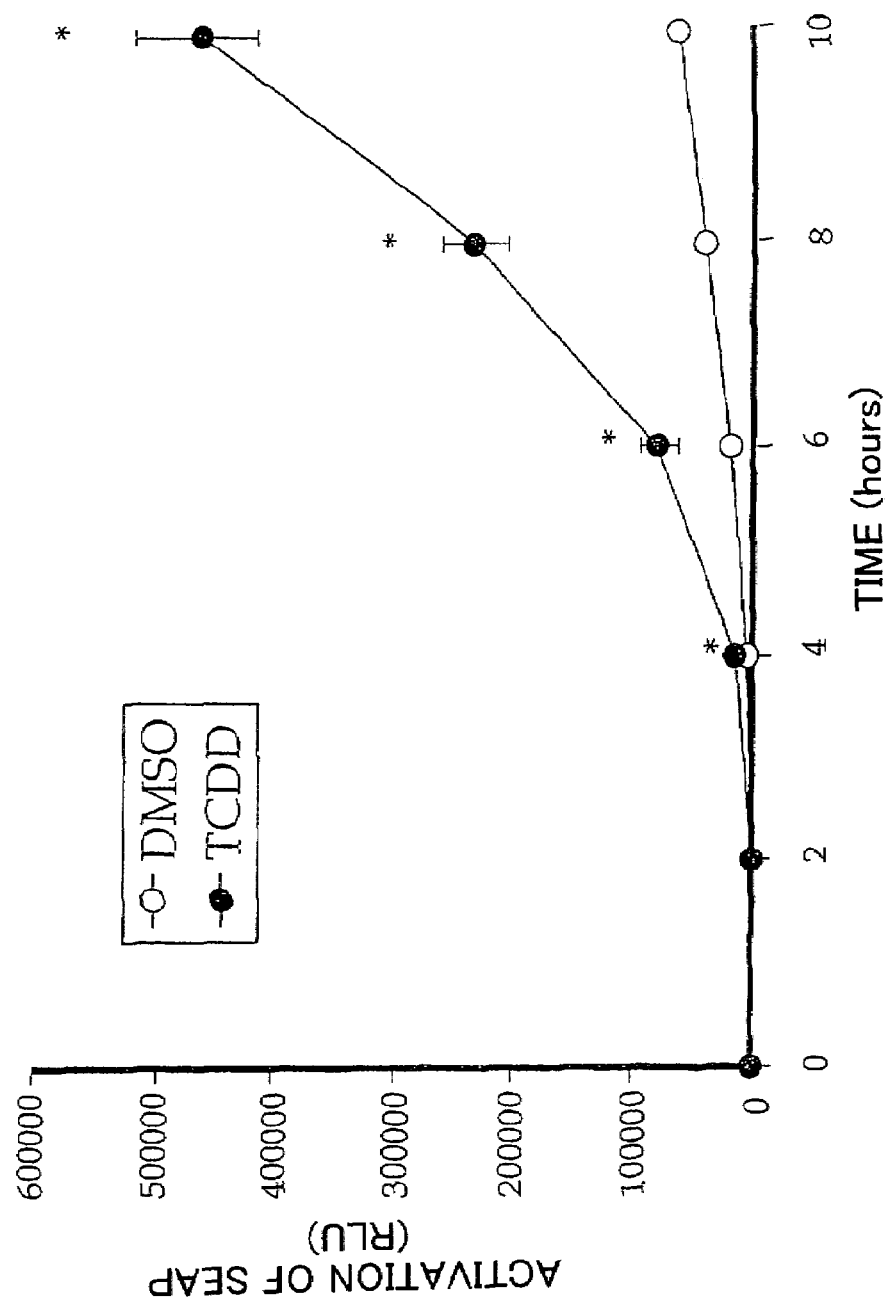
FIG. 7 shows transition (short term) of SEAP protein activity in a conditioned medium after stimulating the HeDS cells with TCDD.
Figure 8:
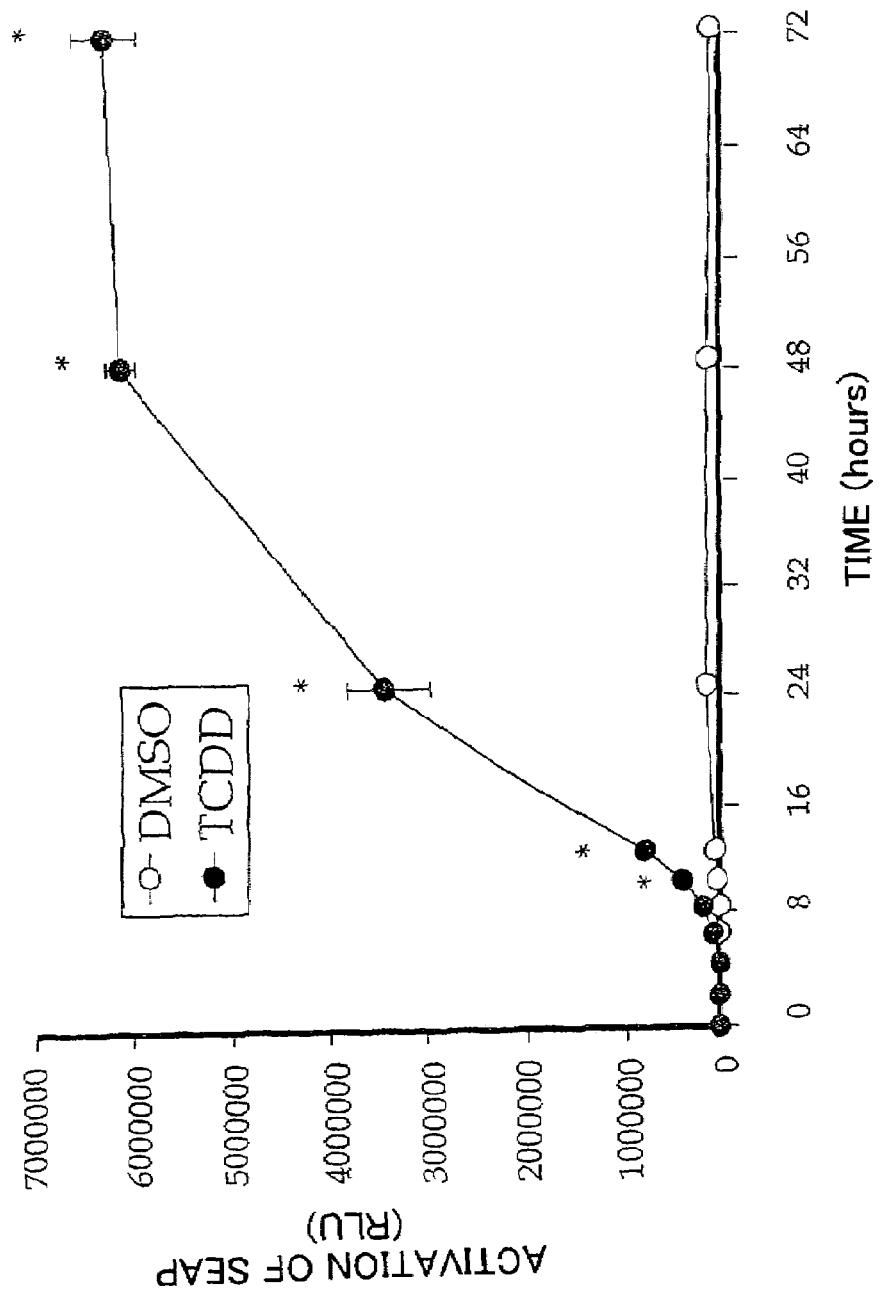
FIG. 8 shows transition (long term) of SEAP protein activity in the conditioned medium after stimulating HeDS cells with TCDD.
Figure 9:
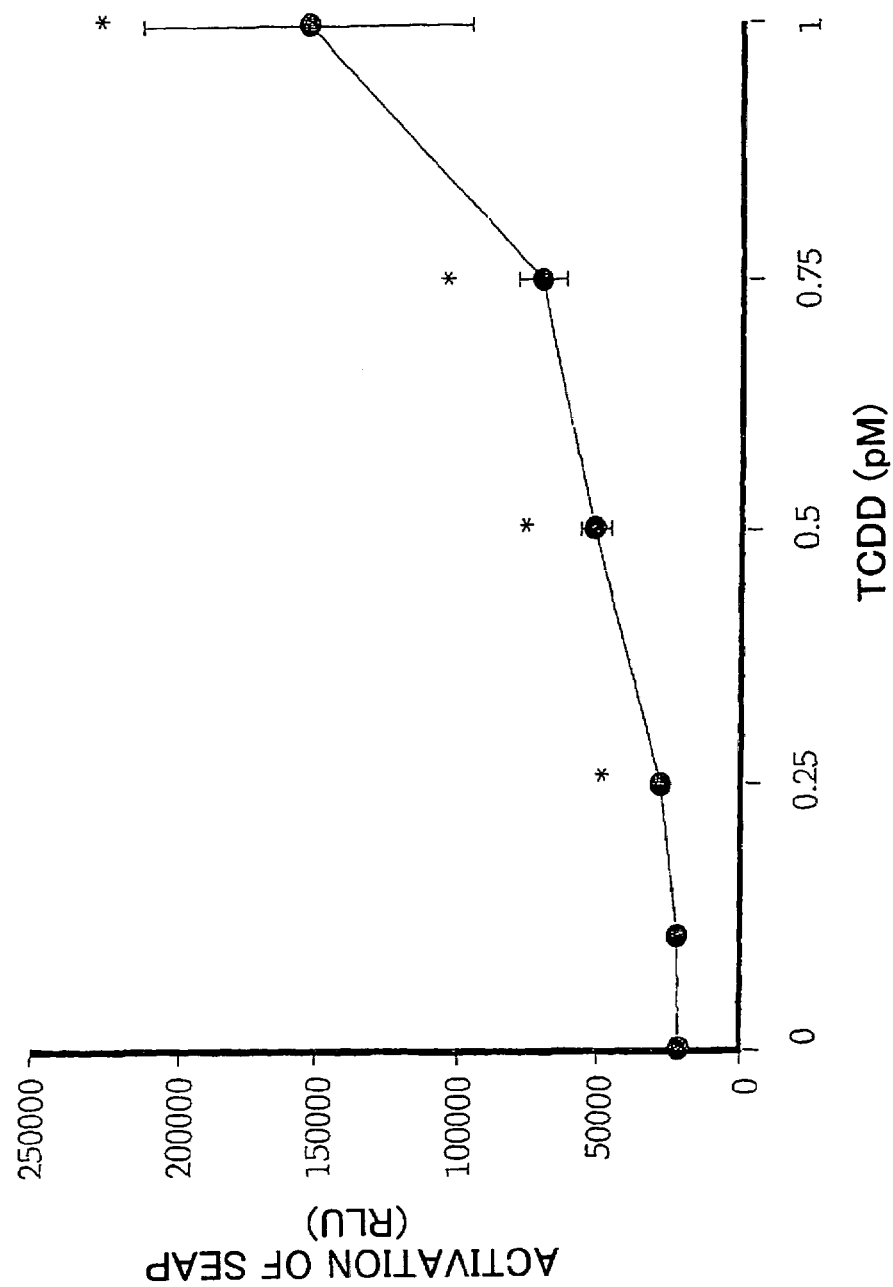
FIG. 9 is a graph showing increases in SEAP protein activity in the conditioned medium when HeDS cells are exposed to TCDD with a low concentration of 0 to 1 pM.
Figure 10:
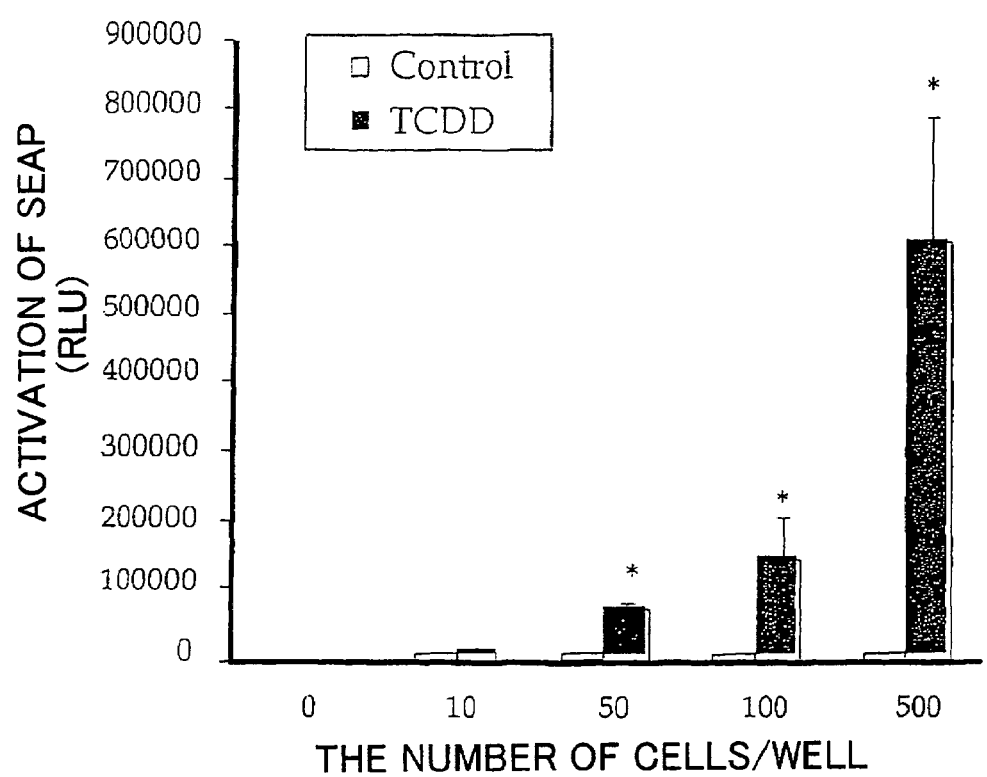
FIG. 10 is a graph showing the number of HeDS cells required for the DRESSA method.
Figure 11:
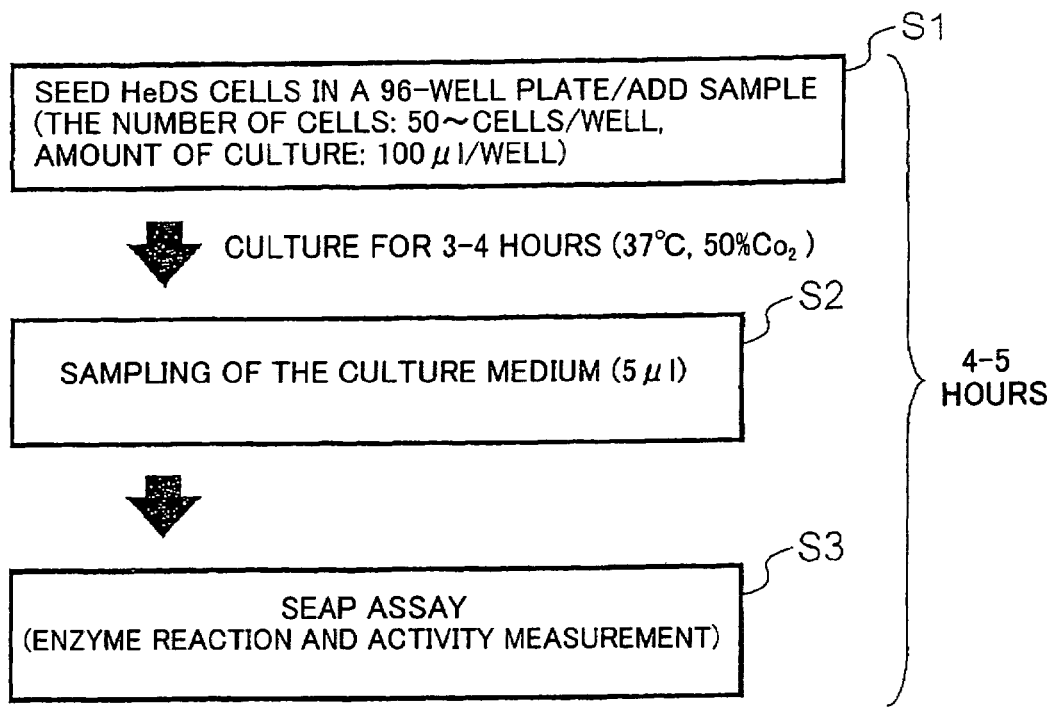
FIG. 11 shows procedures of dioxins sensing by the fast DRESSA method.
Figure 12:
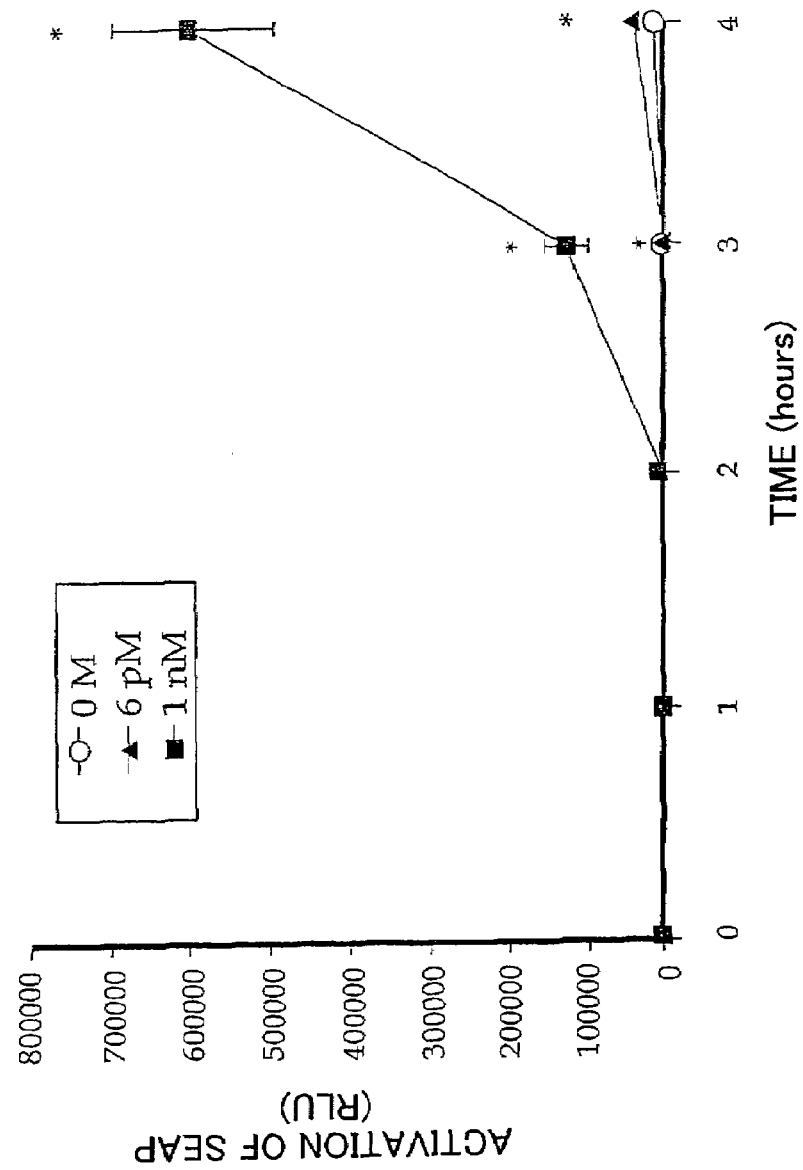
FIG. 12 shows transition of SEAP protein activity in a conditioned medium after stimulating cells with TCDD by the fast DRESSA method.
Figure 13:
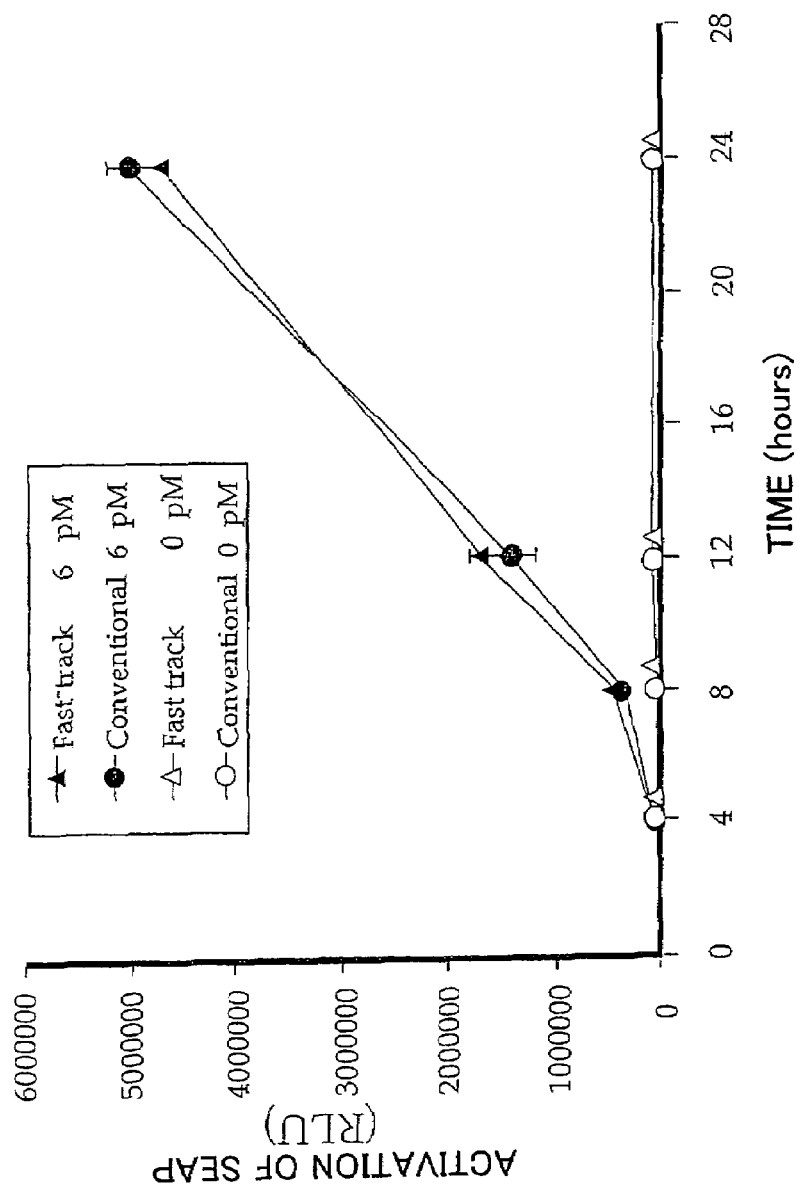
FIG. 13 is a graph showing comparison in sensing sensitivity between the DRESSA method and fast DRESSA method.
Figure 14:
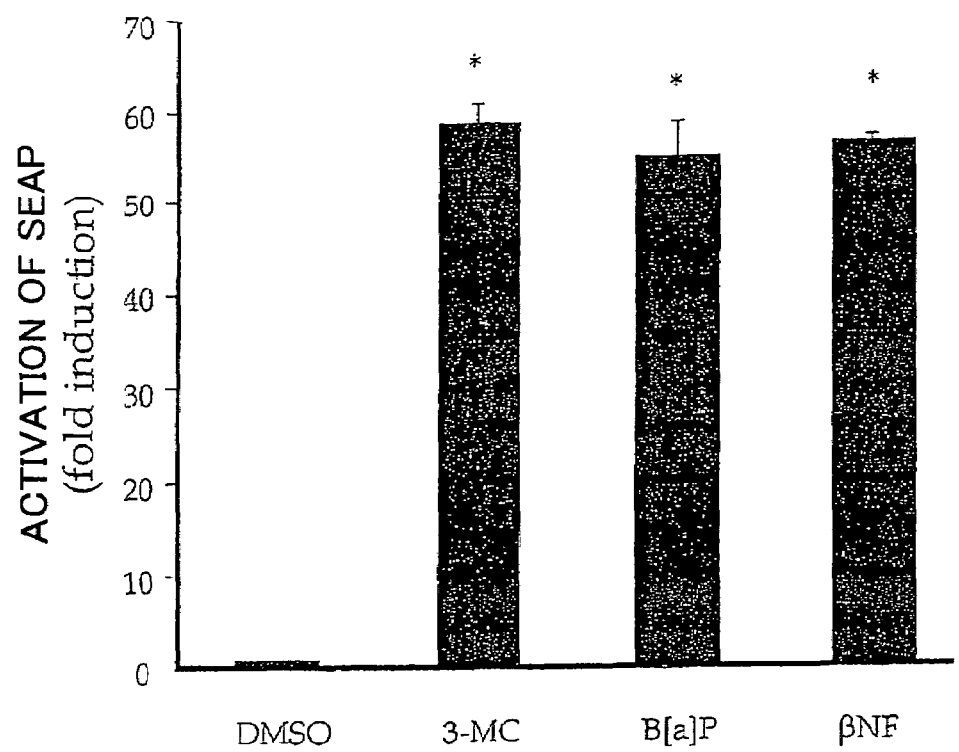
FIG. 14 is a graph showing increases of SEAP protein activity in a conditioned medium after stimulating the HeDS cells with dioxin-like chemical substances.

| Brief Description of Symbols | |
|---|---|
| 1 | HeDS cell |
| 10 | Dioxins responsive plasmid (pDRE-SEAP) |
| 11 | Dioxins high-sensitive gene sequence (MMTV-DRE) |
| 12 | Secreted alkaline phosphatase (SEAP) |
| 13 | Polyadenylation signal (polyA) |

-continued

Brief Description of Symbols

| | |
|---|---|
| 14 | Aryl hydrogen receptor (AhR) |
| 15 | Coactivator (Arnt) |
| 16 | Messenger RNA of SEAP gene |
| 17 | Ribosome |
| 18 | SEAP protein |
| 19 | Secretion of SEAP protein out of the cell |
| 20 | Dioxins |

The invention claimed is:

1. A transgenic cell comprising a plasmid comprising,
a dioxin responsive enhancer (DRE) gene sequence, wherein the DRE gene sequence is integrated into a mouse mammary tumor virus (MMTV) promoter to obtain a MMTV-DRE promoter sequence and
a secreted alkaline phosphatase protein expressing gene disposed downstream of the MMTV-DRE promoter sequence
wherein the MMTV-DRE promoter sequence is inducible upon reaction with dioxins and/or polycyclic aromatic hydrocarbons and
wherein the cell is a Hepa-1c1c7 cell.

2. A biosensor comprising the transgenic cell according to claim 1 wherein the biosensor senses dioxins and/or polycyclic hydrocarbon.

3. A method of sensing dioxins and/or polycyclic aromatic hydrcarbon in a target atmosphere comprising:
placing the transgenic cell according to claim 1 in the target atmosphere;
measuring activity of a secreted alkaline phosphatase protein secreted from the transgenic cell
thereby sensing dioxins and/or polycyclic aromatic hydrocarbon in the target atmosphere.

4. A method of assessing the biological toxicity of tobacco smoke comprising:
contacting the transgenic cell according to claim 1 with tobacco smoke measuring an activity of the secreted alkaline phosphatase protein which the transgenic cell secretes
and thereby assessing the biological toxicity of the tobacco smoke.

5. The transgenic cell according to claim 1, wherein the plasmid comprises two or more DRE sequences.

6. The transgenic cell according to claim 1, wherein the plasmid further comprises a polyadenylation signal disposed downstream of the secreted alkaline phosphatase gene.

* * * * *